United States Patent
Riegler et al.

(10) Patent No.: US 11,255,936 B2
(45) Date of Patent: Feb. 22, 2022

(54) CABLE CONNECTION UNIT FOR CONNECTION TO A GRADIENT COIL UNIT

(71) Applicant: Siemens Healthcare GmbH, Erlangen (DE)

(72) Inventors: Jörg Riegler, Fürth (DE); Simon Bauer, Eggolsheim (DE); Axel Vom Endt, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 91 days.

(21) Appl. No.: 16/743,647

(22) Filed: Jan. 15, 2020

(65) Prior Publication Data

US 2020/0233050 A1   Jul. 23, 2020

(30) Foreign Application Priority Data

Jan. 17, 2019 (DE) .......................... 102019200588.8

(51) Int. Cl.
*G01R 33/385* (2006.01)
*A61B 5/055* (2006.01)

(52) U.S. Cl.
CPC .......... *G01R 33/3858* (2013.01); *A61B 5/055* (2013.01)

(58) Field of Classification Search
CPC ..................... G01R 33/3858; A61B 5/055
See application file for complete search history.

(56) References Cited

U.S. PATENT DOCUMENTS

| | | | | |
|---|---|---|---|---|
| 4,229,615 A * | 10/1980 | Orr, Jr | ................... | H01B 7/083 174/116 |
| 4,356,345 A * | 10/1982 | Gonia | ................. | B29C 66/1122 174/117 F |
| 8,772,636 B2 * | 7/2014 | Yamaguchi | ......... | B60R 16/0215 174/72 A |
| 9,564,256 B2 * | 2/2017 | Manke | ................... | H01B 7/292 |
| 2010/0226058 A1 | 9/2010 | Blakes et al. | | |
| 2016/0141070 A1 | 5/2016 | Heipel et al. | | |
| 2017/0000374 A1 | 1/2017 | O'Neill et al. | | |
| 2017/0371013 A1* | 12/2017 | Stocker | ................ | G01R 33/385 |

FOREIGN PATENT DOCUMENTS

| | | |
|---|---|---|
| CN | 101825693 A | 9/2010 |
| CN | 203150156 U | 8/2013 |
| CN | 105408965 A | 3/2016 |
| CN | 105813556 A | 7/2016 |
| DE | 102016211263 A1 | 12/2017 |

(Continued)

OTHER PUBLICATIONS

Machine Translation of CN 20310156 U, obtained on Jun. 7, 2021 (Year: 2013).*

(Continued)

*Primary Examiner* — Gregory H Curran
(74) *Attorney, Agent, or Firm* — Schiff Hardin LLP

(57) ABSTRACT

Techniques are disclosed relating to a cable connection unit for connection to a gradient coil unit, which includes at least one first electric conductor and one second electric conductor. The first electric conductor and the second electric conductor may be arranged at least partially next to one other, and be connected to one another via a load-carrying connection.

13 Claims, 3 Drawing Sheets

(56) References Cited

FOREIGN PATENT DOCUMENTS

EP    2541709 A2    1/2013
WO    2010003215 A1    1/2010

OTHER PUBLICATIONS

DuPont™ Nomex® N301 Nomex® Aramid Staple Fiber Data Sheet, obtained on Jun. 9, 2021 (Year: 2021).*
Von Andreas, "Textilkabel für Lampen," Radio Kölsch Hamburg; May 20, 2017 // URL: https://www.lampe-bauen.de/textilkabel-fuer-lampen/ with English Translation.
Von Andreas, "Textilkabel Lampe Selber Bauen," Radio Kölsch Hamburg; Apr. 13, 2017; Keine Kommetare, Bauen, Lampen with English Translation.
Chinese Action dated Mar. 17, 2021, Application No. 202010052628.1.
German Action dated Nov. 28, 2019, for Application No. 10 2019 200 588.8.

* cited by examiner

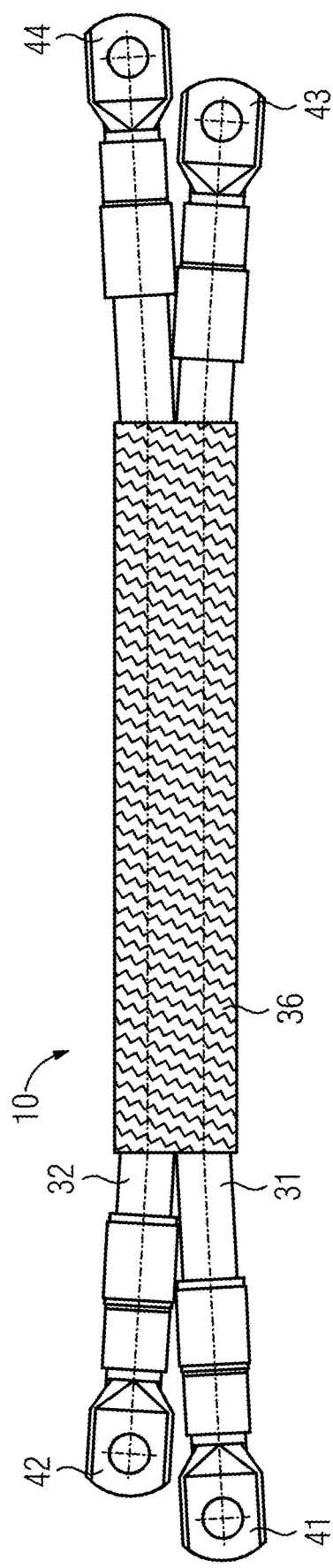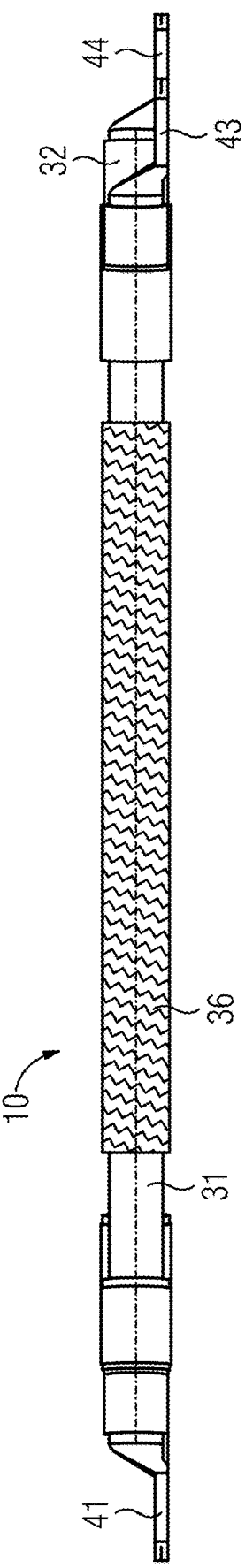
FIG 3
FIG 4

CABLE CONNECTION UNIT FOR CONNECTION TO A GRADIENT COIL UNIT

CROSS-REFERENCE TO RELATED APPLICATIONS

The present application claims the benefit of the filing date of German patent application no. 102019200588.8, filed on Jan. 17, 2019, the contents of which are incorporated herein by reference in their entirety.

TECHNICAL FIELD

The disclosure relates to a cable connection unit for connection to a gradient coil unit and a magnetic resonance device.

BACKGROUND

In a magnetic resonance device, the body to be examined of an examination object, particularly that of a patient, is typically exposed in a patient receiving region to a relatively strong main magnetic field (e.g. 1.5 or 3 Tesla) with the aid of a main magnet. In addition, gradient pulses are output with the aid of a gradient coil unit. By means of a radio-frequency antenna unit, using suitable antenna devices, radio-frequency pulses (RF pulses), particularly excitation pulses, are then emitted, which causes the nuclear spins of particular atoms excited into resonance by these RF pulses to be tilted through a defined flip angle relative to the magnetic field lines of the main magnetic field. When the nuclear spins are relaxed radio-frequency signals, known as magnetic resonance signals, are then emitted, these are received and then further processed using suitable radio-frequency antennas. From the raw data acquired in this way, the desired image data can ultimately be reconstructed.

A gradient coil unit typically comprises three gradient coils. A gradient coil is typically configured to generate a magnetic field gradient in a spatial direction. Gradient coils are controlled using electric currents, the amplitudes of which typically reach several hundreds of amps, and the frequent and rapid changes in current direction are subject to rise and fall rates of several hundred kA/s. Each gradient coil unit, typically each gradient coil, is therefore connected to a gradient control unit. Corresponding electric currents are forwarded to the gradient coil unit by means of the electric connection using a cable connection unit. A cable connection unit typically comprises two electric conductors: a feed conductor and a return conductor. The current flows of the feed and return conductor are typically opposed.

The cable connection unit is typically in the stray field of the main magnetic field and therefore experiences Lorentz forces. This typically results in vibrations during operation of the gradient coil unit. The gradient coil unit itself also experiences vibrations in this context. This can increase the material fatigue and/or reduce the durability of the cable connection unit, in particular in the area of the contact point between the cable connection unit and the gradient coil unit. The vibration during operation of the gradient coil unit can also be transferred to the magnetic resonance device, resulting in a negative impact on the quality of the image data to be generated.

According to conventional systems, a plate of fiber-based laminate or aluminum is provided with a guide groove into which one or more electric conductors are laid. The grooves are filled with epoxy resin to connect the conductor to the plate. However, this method of manufacturing is highly complex, so that a need arises for a cable that is simpler and more economical to manufacture, but which nevertheless withstands the enduring oscillation bending loading. Coaxial cable connection units may also be used. In this context, a flexible conductor is inserted into a rigid pre-bent tube and is fixed in position. The decoupling of the vibration is inadequate in this context, however, due to the rigid design. German patent application publication DE 10 2016 211 263 A1 (US2017/0371013 A1) describes a stabilizing sheathing for a cable connection unit.

SUMMARY

The object underlying the disclosure is to specify a particularly robust and low-vibration cable connection unit. This object is achieved as described herein and further recited in the features of the independent claims. Additional advantageous embodiments are further described in the dependent claims.

As described in further detail herein, embodiments of the cable connection unit for connection to a gradient coil unit include at least one first electric conductor and one second electric conductor. Further in accordance with such embodiments, the first electric conductor and the second electric conductor are arranged at least partially next to each other and are connected to one another via a load-carrying connection.

The first electric conductor and/or the second electric conductor are preferably embodied longitudinally. The first electric conductor and/or the second electric conductor may have any suitable cross-sectional area. For example, first electric conductor and/or the second electric conductor may have a cross-sectional area between 35 mm$^2$ and 150 mm$^2$, between 50 and 120 mm$^2$, between 70 mm$^2$ and 100 mm$^2$, etc. The cross-section of the first electric conductor and/or of the second electric conductor may be circular or rectangular. The first electric conductor and the second electric conductor may be arranged next to each other parallel to their longitudinal axis. The first electric conductor and the second electric conductor may be arranged at least partially in parallel. The first electric conductor and the second electric conductor may be arranged next to each other and/or parallel to one another such that the first electric conductor and the second electric conductor have any suitable length relative to one another. For instance, the first electric conductor and the second electric conductor may be at least 70% of the length of the shorter electric conductor of the first electric conductor and of the second electric conductor, at least 85% of the length of the shorter electric conductor of the first electric conductor and of the second electric conductor, etc. In various embodiments, the length of the first electric conductor and of the second electric conductor may differ from one another by a maximum of 30%, by a maximum of 15%, etc.

A load-carrying connection produces a frictional (i.e. friction-fit) connection. A load-carrying connection is typically achieved as a result of static friction between at least one additional component and the components to be connected, in particular as a result of static friction between at least one additional component and the first electric conductor and the second electric conductor. The first electric conductor may be the feed conductor for connection to the gradient coil unit. The second electric conductor may be the return conductor for connection to the gradient coil unit. The first electric conductor and the second electric conductor may be electrically conductively connected to one another via the gradient coil unit and/or a gradient coil included in the gradient coil unit.

An advantage of the cable connection unit embodiments described herein is that it is a particularly robust and low-vibration. The arrangement of the first electric conductor and of the second electric conductor at least partially next to each other, and in particular at least partially parallel to one another, facilitates a reduction and/or partial compensation of the Lorentz forces. The frictional connection also contributes to a reduction and/or at least partial compensation of the Lorentz forces. The frictional connection and the ensuing frictional coupling of the first electric conductor and of the second electric conductor does not typically impair the compensation of the Lorentz forces. The cable connection unit embodiments described herein are typically free of a rigid body, and can be implanted flexibly. This reduces vibrations in the cable connection unit. The cable connection unit embodiments described herein do not transfer any vibrations (or transfer only minimal vibrations) to the gradient coil unit and/or to the magnetic resonance device. As a result, the quality of the acquired raw data is improved. The wear and tear of material is also reduced as a result of the reduced vibration and/or the increased flexibility of the cable connection unit. In particular, the part of the cable connection unit which is embodied for direct connection to the gradient coil unit, i.e. for example a contact point or a cable lug, is subjected to lower vibrations, and therefore to reduced wear and tear, which in turn reduces material fatigue. The cable connection unit embodiments described herein also provide an improved decoupling of the cable connection unit from the gradient coil unit.

One embodiment of the cable connection unit provides that the cable connection unit comprises a cladding which encloses the first electric conductor and the second electric conductor in an arrangement next to one another. The first electric conductor and the second electric conductor in an arrangement next to one another can be designated as an arrangement of electric conductors.

The cladding is preferably embodied tubularly and/or longitudinally. The cladding may have a hollow space which corresponds at least approximately to the cross-section of the arrangement of electric conductors. The cladding may be arranged on the outer circumference of the arrangement of electric conductors. The cladding may follow the contour and/or the circumference of the arrangement of electric conductors, with the exception of concave indentations and/or with the exception of hollow spaces. The cladding may enclose the arrangement of electric conductors at least partially in a longitudinal direction. In the arrangement which encloses the arrangement of electric conductors, the cross-section of the cladding corresponds at least approximately to the cross-section of the arrangement of electric conductors. In the arrangement which encloses the arrangement of electric conductors, the cross-section of the cladding deviates by a maximum of 20%, preferably by a maximum of 10% from the cross-section of the arrangement of electric conductors.

The cladding may be in direct connection with the arrangement of electric conductors. In particular, a connection between the arrangement of electric conductors and the cladding may be a friction-fir connection, i.e. based on static friction, and may be exclusively based on static friction between the arrangement of electric conductors and the cladding. The cladding may loosely enclose the arrangement of electric conductors, in particular without a further aid for fixing the cladding to the arrangement of electric conductors. In this way, the cladding stabilizes the arrangement of electric conductors without increasing the rigidity of the cable connection unit and/or reducing the flexibility of the cable connection unit. The cladding can limit a movement of the first electric conductor and/or of the second electric conductor due to an electric current and/or a Lorentz force. This reduces wear and tear of the material. The cladding typically retains the flexibility of the arrangement of the cable connection unit. A cable connection unit of this type is both particularly robust and is low in complexity. This enables a particularly durable embodiment and simple maintenance of the cable connection unit.

One embodiment of the cable connection unit provides that the cladding is embodied in such a way that it effects the load-carrying connection on the arrangement of the first electric conductor and of the second electric conductor next to one another. The cladding may be implemented in such a way that it effects a force perpendicular to the longitudinal axis of the arrangement of electric conductors next to one another. This force may be based on static friction. A cable connection unit of this type is particularly advantageous as there is no need in particular for a form fit, and the flexibility of the cable connection unit is not impaired. The cladding can in particular be implemented in such a way that the load-carrying connection is effected upon movement and/or extension in the case of at least one electric conductor of the first electric conductor or of the second electric conductor. In particular, the load-carrying connection can become greater in the event of increasing movement of the arrangement of electric conductors. This improves the functionality of the cable connection unit. In the event of movement of the arrangement of electric conductors, the effect of the cladding is limiting and/or stabilizing, whereas in the idle state the flexibility of the arrangement of electric conductors is greater. A further advantage of this embodiment is a reduction in the complexity of the cable connection unit due to the particularly advantageous arrangement of the cladding.

One embodiment of the cable connection unit provides that the cladding comprises a textile material, which may comprise fibers, for example. The textile material may, for example, comprise aramids, such as aramid fibers.

A cladding of this type can enclose the arrangement of electric conductors in a particularly flush manner. Textile material is sufficiently flexible for an enclosing arrangement in relation to the arrangement of electric conductors. Textile material also has a high tear strength, so that a high force in relation to the arrangement of the electric conductors can be achieved by means of static friction, i.e. a particularly effective load-carrying connection. Textile material also has a coefficient of friction which, on the one hand facilitates a load-carrying connection and, on the other hand, gives more space and/or flexibility to the arrangement of electric conductors in the case of minimal movement and/or minimal extension. A further advantage of this embodiment is a reduction in the complexity of the cable connection unit due to the materials used.

One embodiment of the cable connection unit provides that the cladding is embodied as heat-shrink tubing. One embodiment of the cable connection unit provides that the cladding is embodied as flame-retardant.

One embodiment of the cable connection unit provides that the cladding is a braid and/or wrapping. For instance, textile material can be wound particularly well around the arrangement of electric conductors. This allows a simple and effective structural design of the cable connection unit.

One embodiment of the cable connection unit provides that the cladding has a tensile strength of any suitable range.

For instance, the cladding may have a tensile strength of at least 5 Megapascal (MPa), of at least 8 MPa, of at least 11 MPa, etc. The aforementioned tensile strength may relate, for example, to a tensile strength determined according to American Society for Testing and Materials (ATSM) ASTM-D 638.

One embodiment of the cable connection unit provides that the cladding has an elongation at break of any suitable range. For instance, the cladding may have an elongation at break of at least 320%, of at least 380%, of at least 420%, etc. The aforementioned elongation at break may relate, for example, to an elongation at break determined according to ASTM-D 638. A cladding of this type may be particularly suitable as, on the one hand, it can exert sufficient force perpendicular to the arrangement of electric conductors and, on the other hand, it can provide the arrangement of electric conductors with sufficient flexibility. In particular, sufficient flexibility can be granted during operation of the gradient coil unit and/or when idle.

One embodiment of the cable connection unit provides that the cable connection unit is at least 30 cm long and may be various proportions of the 30-cm-long end section of the cable connection unit, which can be connected to the gradient coil unit having the cladding. This proportion may be least 70%, of the 30-cm-long end section of the cable connection unit between 50% and 90%, between 60% and 80%, between 65% and 75% of the 30-cm-long end section of the cable connection unit, etc. The end section of the cable connection unit, which can be connected to the gradient coil unit, is typically characterized in that this is delimited on one side by the longitudinal end of the cable connection unit, said longitudinal end being designed to be connected to the gradient coil unit. The length of the end section typically relates to a distance along the longitudinal axis of the cable connection unit starting from this longitudinal end. The cable connection unit may be any suitable length such as at least 30 cm, at least 40 cm, etc. The cable connection unit may have any suitable maximum length such as, for instance, 3 m, 2.5 m, 1.2 m, etc.

The cladding may enclose the arrangement of electric conductors via at least one subsection and/or subarea of the longitudinal extension. The cladding may encloses the arrangement of electric conductors end-to-end, in particular free of interruptions. The cladding may enclose end-to-end and/or continuously at least 70% of the 30 cm end section of the cable connection unit which can be connected to the gradient coil unit. In this way, the cladding can reduce the vibration of the cable connection unit and/or of the arrangement of electric conductors particularly well.

One embodiment of the cable connection unit provides that at a portion of the cable connection unit length, starting from the end to be connected to the gradient coil unit, be free of cladding. This cladding free length may be, for example, at least 7 cm, at least 10 cm, etc. The end to be connected to the gradient coil unit corresponds to the longitudinal end of the cable connection unit, which is designed to be connected to the gradient coil unit. This embodiment allows a good connection of the cable connection unit to the gradient coil unit.

One embodiment of the cable connection unit provides that the first electric conductor and the second electric conductor are connected to one another by means of an elastic material. The elastic material may be, for example, electrically insulating. The elastic material may preferably not be electrically conductive. The elastic material may comprise an adhesive. The elastic material connects the first electric conductor to the second electric conductor. The elastic material may thus connect the first electric conductor to the second electric conductor adhesively, provided that no external force, in particular no force generated by a current flow in the first electric conductor or the second electric conductor, impacts the arrangement of electric conductors. The elastic material may be implemented in such a way that the arrangement of electric conductors is retained when the cable connection unit does not conduct any electric current, e.g. independently of the cladding.

The first electric conductor and the second electric conductor may be at least partially enclosed by the elastic material.

The elastic material may comprise, for example, silane-modified polymers (SMP). For example, the elastic material can be an SMP glue jointing compound. The elastic material may have any suitable range of viscosities. For instance, the elastic material may have a viscosity between 700 Pa*s and 1300 Pa*s, between 850 Pa*s and 1150 Pa*s, between 950 Pa*s and 1050 Pa*s, etc. The viscosity may relate in this context, for example, to a viscosity determined at 23° C. and 55% air humidity. The elastic material may have any suitable range of tensile strengths, such as between 1.3 N/mm$^2$ and 3 N/mm$^2$, between 1.7 N/mm$^2$ and 2.6 N/mm$^2$, between 2.1 N/mm$^2$ and 2.3 N/mm$^2$, etc. The tensile strength may relate in this context, for instance, to a tensile strength determined according to the German Institute for Standardization (DIN) 53504.

If the arrangement of electric conductors has a concave shape, as is the case for example with an arrangement of two circular electric conductors next to one another, the elastic material can at least partially fill the concave shape. The elastic material can connect the first electric conductor and the second electric conductor to one another in such a way that the first electric conductor and the second electric conductor adjoin each other directly, as can be embodied for example in the case of an at least partial filling of at least one concave shape. The elastic material can connect the first electric conductor and the second electric conductor to one another in such a way that the elastic material prevents a direct contact between the first electric conductor and the second electric conductor, therefore at each position of the cable connection unit, there is either space or the elastic material between the first electric conductor and the second electric conductor. The elastic material can form a detachable or a non-detachable connection between the first electric conductor and the second electric conductor.

The advantage of this embodiment is a stable arrangement of electric conductors, which is both flexible and therefore low in vibration at the same time. In combination with the cladding, the cable connection unit allows a particularly good frictional and flexible connection, which is low in vibration and flexible during operation of the gradient coil unit, and which also retains its shape and/or arrangement when idle. This embodiment is consequently particularly robust.

One embodiment of the cable connection unit provides that the first electric conductor and the second electric conductor each have at least one cable lug for connection to the gradient coil unit. This allows a cost-effective and simple use of the cable connection unit.

One embodiment of the cable connection unit provides that the first electric conductor and/or the second electric conductor each have an insulation and a stranded conductor. This removes the need for a coaxial cable. Furthermore, this cable connection unit can be produced in a particularly cost-effective manner using commercially-available electric conductors. However, this embodiment allows a compensation of the Lorentz forces.

The disclosure also assumes a magnetic resonance device comprising a gradient coil unit and a cable connection unit according to one of the described embodiments for connection to the gradient coil unit. The cable connection unit may be connected to the gradient coil unit in a detachable manner. The cable connection unit may connect the gradient coil unit to the gradient amplifier and/or a connection plate in a detachable manner.

The advantages of the embodiments of the magnetic resonance device essentially correspond to the advantages of the embodiments of the cable connection unit, which are explained above in detail. Features, advantages or alternative embodiments mentioned herein can also be transferred to the other claimed subject matter, and vice versa.

BRIEF DESCRIPTION OF THE DRAWINGS/FIGURES

Further advantages, features and details of the disclosure will become apparent from the exemplary embodiments described below as well as with reference to the drawings, in which:

FIG. 3 shows a schematic representation of a cable connection unit for connection to a gradient coil unit in a second view, in accordance with an embodiment of the present disclosure;

FIG. 4 shows a schematic representation of a cable connection unit for connection to a gradient coil unit in a third view, in accordance with an embodiment of the present disclosure.

DETAILED DESCRIPTION

Figure 1:
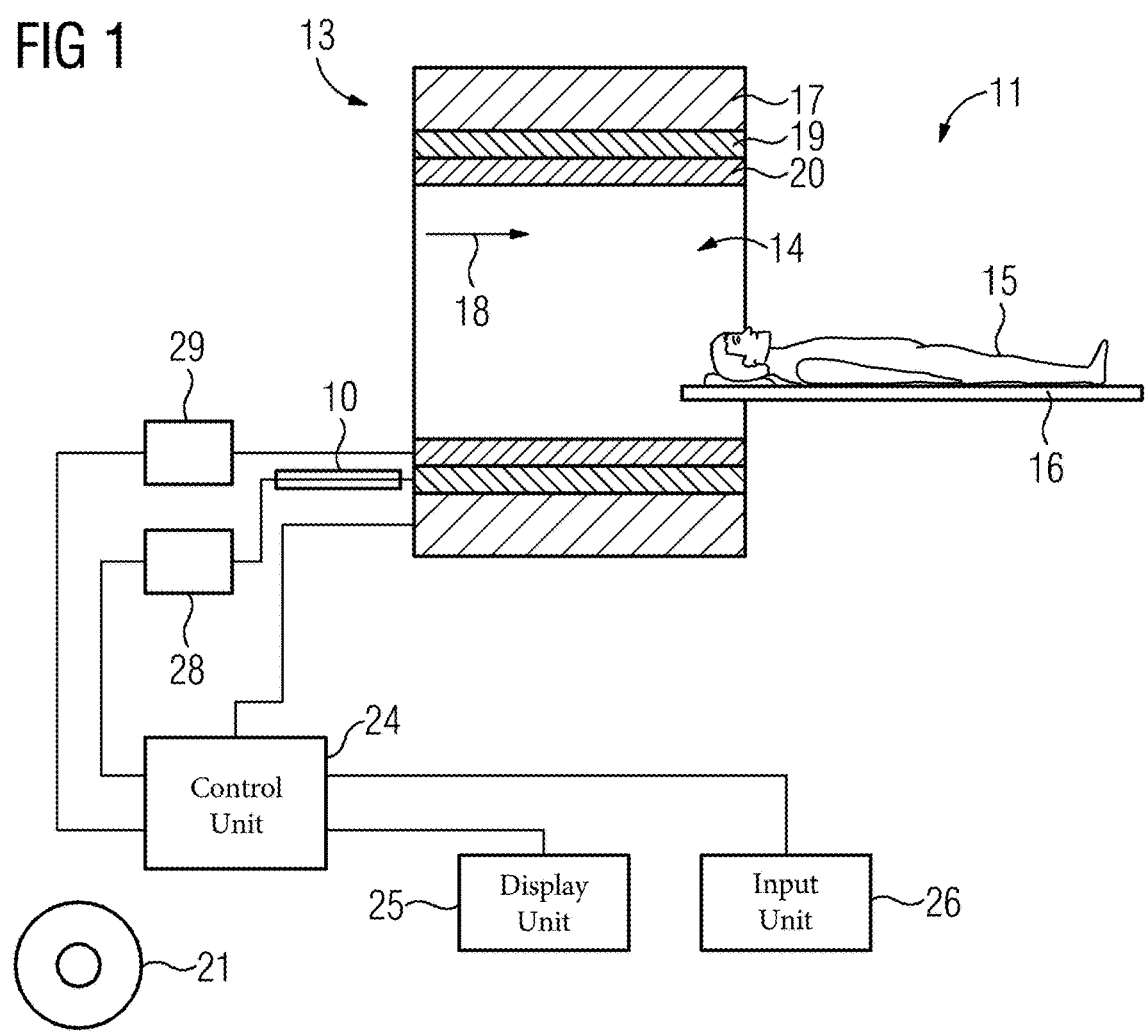
FIG. 1 shows a magnetic resonance device in a schematic representation, in accordance with an embodiment of the present disclosure.

FIG. 1 shows a magnetic resonance device 11 in a schematic representation. The magnetic resonance device 11 comprises a detector unit including a magnet unit 13 with a main magnet 17 for generating a strong and constant main magnetic field 18. Furthermore, the magnetic resonance device 11 has a cylindrical patient receiving region 14 for accommodating a patient 15, wherein the patient receiving region 14 is cylindrically enclosed in a peripheral direction by the magnet unit 13. The patient 15 can be pushed by means of a patient support apparatus 16 of the magnetic resonance device 11 into the patient receiving region 14. For this purpose, the patient support apparatus 16 has a patient couch which is arranged movably within the magnetic resonance device 11.

The magnet unit 13 also has a gradient coil unit 19, which is used for position encoding during an imaging process. The gradient coil unit 19 is operated by means of a gradient control unit 28. The gradient control unit 28 typically comprises a gradient amplifier. The gradient control unit 28 is at least partially connected to the gradient coil unit 19 by means of a cable connector that is shown as the cable connection unit 10. Furthermore, the magnet unit 13 has a radio-frequency antenna unit 20 which, in the case shown, is configured as a body coil permanently integrated into the magnetic resonance device 11, and a radio-frequency antenna control unit 29 for an excitation of a polarization which occurs in the main magnetic field 18 generated by the main magnet 17. The radio-frequency antenna unit 20 is operated by the radio-frequency antenna control unit 29 and radiates radio-frequency pulses into an examination space which is substantially formed by the patient receiving region 14.

For the purpose of controlling the main magnet 17, the gradient control unit 28 and the radio-frequency antenna control unit 29, the magnetic resonance device 11 has a control unit 24. The control unit 24 centrally controls the magnetic resonance device 11, for example, the execution of MR control sequences. Furthermore, the control unit 24 comprises a reconstruction unit (not shown in detail) for reconstructing medical image data which is acquired during the magnetic resonance examination. The magnetic resonance device 11 has a display unit 25. Control information such as, for example, control parameters and reconstructed image data can be displayed on the display unit 25, for example on at least one monitor for a user. In addition, the magnetic resonance device 11 has an input unit 26 by means of which information and/or control parameters can be input by a user during a scanning procedure. The control unit 24 can comprise the gradient control unit 28 and/or the radio-frequency antenna control unit 29 and/or the display unit 25 and/or the input unit 26.

The control unit 24 has computer programs and/or software, which can be directly loaded into a storage unit of the control unit 24 not shown in further detail, having program means in order to actuate the gradient control unit 28 and/or the radio-frequency antenna control unit 29 when the computer programs and/or software are executed in the control unit 24. For this purpose, the control unit 24 has a processor (not disclosed in further detail) which is configured to execute the computer programs and/or software. Alternatively, the computer programs and/or software can also be stored on an electronically readable data carrier 21 configured separately from the control unit 24, wherein a data access by the control unit 24 can take place on the electronically readable data carrier 21 via a data network.

The magnetic resonance device 11 as shown can comprise additional, less, or alternate components which magnetic resonance devices 11 typically have. A general mode of operation of a magnetic resonance device 11 is also known to the person skilled in the art, so that a detailed description of the further components is not included.

Figure 2:
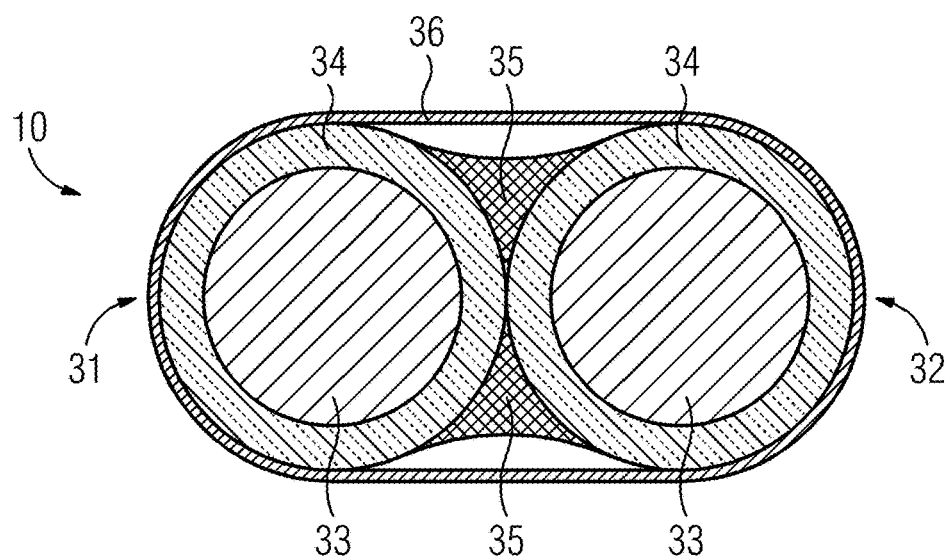
FIG. 2 shows a schematic representation of a cable connection unit for connection to a gradient coil unit in a first view, in accordance with an embodiment of the present disclosure.

FIG. 2 shows a schematic representation of a cable connection unit 10 for connection to a gradient coil unit 19 in a first view. The cable connection unit 10 comprises a first electric conductor 31 and a second electric conductor 32. The first electric conductor 31 and the second electric conductor 32 each comprise an insulation 34 and a stranded conductor 33. The first electric conductor 31 and the second electric conductor 32 are arranged next to each other. The first electric conductor 31 and the second electric conductor 32 may be connected to one another by means of an elastic material 35, which typically stabilizes the arrangement of the electric conductors in the idle state.

The first electric conductor 31 and the second electric conductor 32 are connected to one another by means of a load-carrying connection (e.g. a friction-fit connection). The load-carrying connection is effected by the cladding 36, which encloses the first electric conductor 31 and the second electric conductor 32. The cladding 36 may be implemented, for example, as a wrapping made from a textile material. The cladding 36 may not have any fixing to the first electric conductor 31 and/or the second electric conductor 32. The cladding 36 stabilizes the arrangement of the first electric conductor 31 and of the second electric conductor 32 typically by means of static friction. The cladding 36 typically has a tensile strength of at least 5 MPa.

FIG. 3 shows a schematic representation of a cable connection unit 10 for connection to a gradient coil unit 19 in a second view, which is orthogonal to the first view in FIG. 2. In this view, it is evident that the first electric conductor 31 and the second electric conductor 32 are arranged next to one another, largely in parallel. The first electric conductor 31 and the second electric conductor 32 each have two cable lugs 41, 42, 43, 44. Two cable lugs 41, 42 arranged at the same end of the cable connection unit 10 are designed for connection to the gradient coil unit 19. Two cable lugs 43, 44 arranged at the opposite end of the cable connection unit 10 are designed for connection to the gradient control unit 28 and/or to a connecting plate comprised by the gradient control unit 28. The gradient control unit 28 can comprise a gradient amplifier and/or a connecting plate. The cable connection unit 10 may connect the gradient coil unit 19 to a connecting plate, the spatial distance of which to the gradient coil unit 19 may be any suitable distance, such as for example less than 2 meters, less than 1.5 meters, less than 1 meter, etc. The connecting plate may be connected to one of the gradient amplifiers comprised in the gradient control unit 28 by means of a cable connection.

FIG. 4 shows a schematic representation of a cable connection unit 10 for connection to a gradient coil unit 19 in a third view, which is orthogonal to the first view in FIG. 2 and to the second view in FIG. 3.

Figure 5:
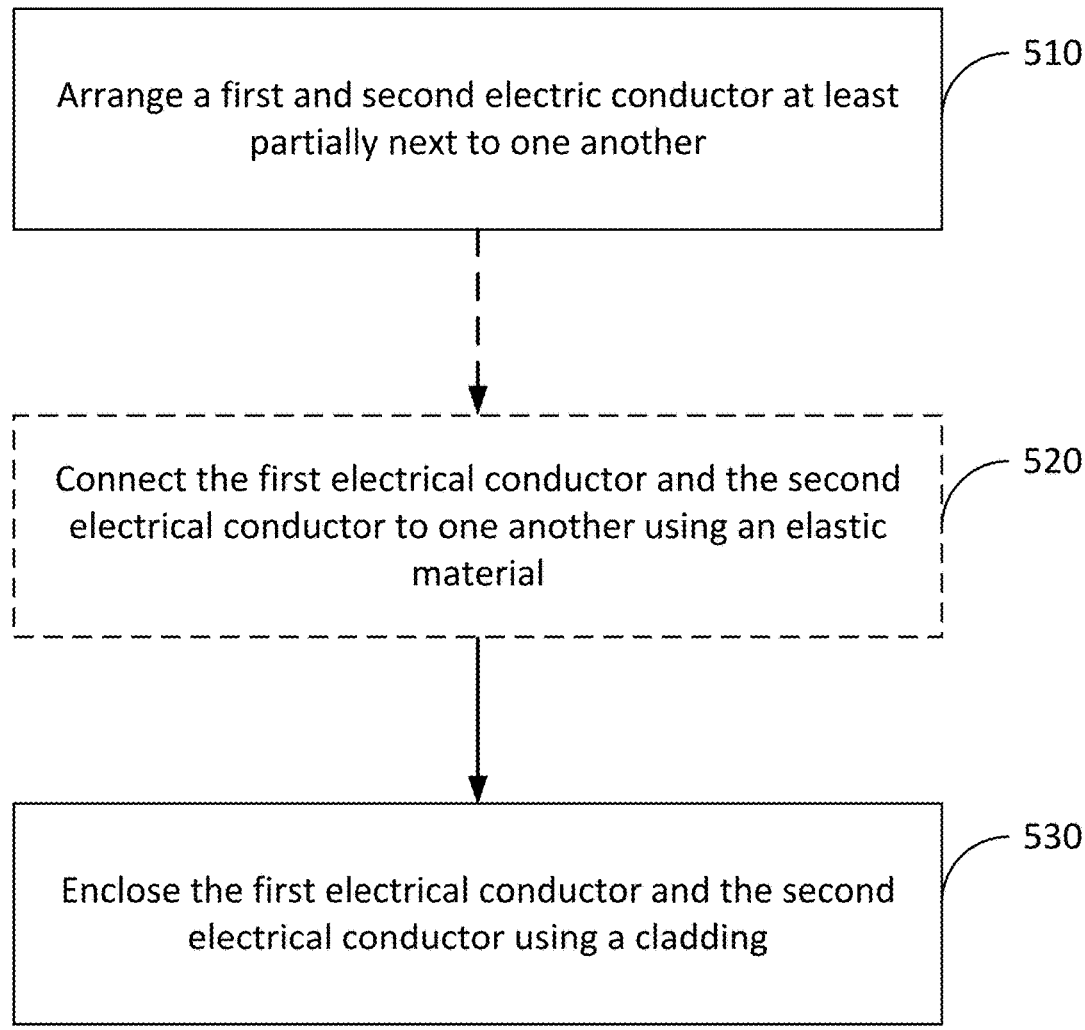
FIG. 5 shows a block diagram of a method for manufacturing a cable connection unit for operating a gradient coil unit in accordance with an embodiment of the present disclosure.

FIG. 5 shows a block diagram of a method for manufacturing a cable connection unit 10 for connection to a gradient coil unit 19. In the method 500, a first electric conductor 31 and a second electric conductor 32 are at least partially arranged (block 510) next to one another. Optionally, the method 500 includes the first electric conductor 31 being connected (block 520) to the second electric conductor 32 by means of an elastic material 35. The method 500 also includes the first electric conductor 31 and the second electric conductor 32 being enclosed (block 530) in an arrangement next to one another by means of a cladding 36, establishing a load-carrying connection between the first electric conductor 31 and the second electric conductor 32.

Although the disclosure has been illustrated and described in detail by the exemplary embodiments, the disclosure is not restricted by the examples disclosed herein, and other variations can be derived therefrom by a person skilled in the art without departing from the protective scope of the disclosure.

What is claimed is:

1. A cable connector for connecting to a set of gradient coils of a magnetic resonance device, the cable connector comprising:
   at least one first electric conductor;
   at least one second electric conductor;
   a cladding comprising a textile material that encloses the first electric conductor and the second electric conductor; and
   an elastic material that connects the first electric conductor and the second electric conductor to one another to retain an arrangement of the first electric conductor and the second electric conductor independently of the cladding,
   wherein the first electric conductor and the second electric conductor are arranged at least partially next to one other and are connected to one another via a friction-fit connection that is formed based exclusively on static friction between the (i) first electric conductor and the second electric conductor, and (ii) the cladding.

2. The cable connector as claimed in claim 1, wherein the cladding is a braid or a wrapping.

3. The cable connector as claimed in claim 1, wherein the cladding has a tensile strength of at least 5 Megapascals (MPa).

4. The cable connector as claimed in claim 1, wherein the cable connector has a length of at least 30 cm, and
   wherein at least 70% of the 30-cm length of the cable connector that is configured to be connected to the set of gradient coils includes the cladding.

5. The cable connector as claimed in claim 1, wherein at least 7 cm of the cable connector, from the end that is configured to be connected to the set of gradient coils, is free of the cladding.

6. The cable connector as claimed in claim 1, wherein the first electric conductor and the second electric conductor each have at least one cable lug for connection to the set of gradient coils.

7. The cable connector as claimed in claim 1, wherein at least one of the first electric conductor and the second electric conductor has (i) an insulation, and (ii) a stranded conductor.

8. The cable connector as claimed in claim 1, wherein the first electric conductor and the second electric conductor are arranged parallel to one another.

9. The cable connector of claim 1, wherein the elastic material comprises an adhesive that connects the first electric conductor to the second electric conductor.

10. The cable connector of claim 1, wherein the elastic material partially fills a space between (i) the first electrical conductor and the second electrical conductor, and (ii) the cladding.

11. The cable connector of claim 1, wherein the elastic material forms a detachable connection between the first electric conductor and the second electric conductor.

12. The cable connector of claim 1, wherein the friction-fit connection formed between the first electric conductor and the second electric conductor reduces an effect of Lorentz forces as a result of the cable connector being disposed in a stray field of a main magnetic field of the magnetic resonance device.

13. A magnetic resonance device, comprising:
   a set of gradient coils forming a gradient coil unit; and
   a cable connector configured to connect to the gradient coil unit, the cable connector including:
      at least one first electric conductor;
      at least one second electric conductor;
      a cladding comprising a textile material that encloses the first electric conductor and the second electric conductor; and
      an elastic material that connects the first electric conductor and the second electric conductor to one another to retain an arrangement of the first electric conductor and the second electric conductor independently of the cladding;
   wherein the first electric conductor and the second electric conductor are arranged at least partially next to one other and are connected to one another via a friction-fit connection that is formed based exclusively on static friction between the (i) first electric conductor and the second electric conductor, and (ii) the cladding.

\* \* \* \* \*